United States Patent [19]

Collins et al.

[11] Patent Number: 5,201,719

[45] Date of Patent: Apr. 13, 1993

[54] DISPOSABLE HYPODERMIC NEEDLE AND MEDICATION CATRIDGE

[76] Inventors: Cary C. Collins, P.O. Box 4104, 4104 Garth Rd., SE., Huntsville, Ala. 35802; Robert L. Kurtz, P.O. Box 12213, 2619 Gawain Rd., SE., Huntsville, Ala. 35815

[21] Appl. No.: 695,718

[22] Filed: May 6, 1991

[51] Int. Cl.$^5$ .............................................. A61M 5/32
[52] U.S. Cl. ................................. 604/195; 604/196; 604/218; 604/227; 604/110; 128/919
[58] Field of Search ........ 604/110, 192, 187, 194–198, 604/218, 227, 232; 128/919

[56] References Cited

U.S. PATENT DOCUMENTS

| | | | |
|---|---|---|---|
| 877,946 | 2/1908 | Overton | 604/194 |
| 4,664,653 | 5/1987 | Sagstetter et al. | 604/197 |
| 4,767,413 | 8/1988 | Haber et al. | 604/198 |
| 4,813,936 | 3/1989 | Schroeder | 604/195 |
| 4,822,340 | 4/1989 | Kamstra | 604/135 |
| 4,957,490 | 9/1990 | Byrne et al. | 604/197 |
| 5,098,382 | 3/1992 | Haber et al. | 604/110 |
| 5,125,908 | 6/1992 | Cohen | 604/196 |
| 5,135,510 | 8/1992 | Maszkiewicz et al. | 604/195 |
| 5,167,641 | 12/1992 | Schmitz | 604/196 |

FOREIGN PATENT DOCUMENTS

| | | | |
|---|---|---|---|
| 0164214 | 3/1955 | Australia | 604/196 |
| 0700846 | 1/1966 | Italy | 604/195 |

*Primary Examiner*—C. Fred Rosenbaum
*Assistant Examiner*—Mark O. Polutta
*Attorney, Agent, or Firm*—Jennings, Carter, Thompson & Veal

[57] ABSTRACT

A reusable hypodermic syringe assembly (200) comprising a syringe (218) having a barrel shaped portion (214) with an opening (280) therein, a cartridge (202) insertable into and removable from the barrel shaped portion (214) of the syringe and containing a medication (262) into a patient from the cartridge (202) with the needle (210) and the medication (262) being sealably contained within first (204) and second (260) separately sealed compartments, respectively, within the cartridge (202) before injection of the medication. A plunger (224) functions to push on the second compartment (204) and thereby extends the distal end of the needle (210) out of the cartridge (202) and the proximal end of the needle (213) into the sealed second compartment (204) containing the medication before the injection of the medication (262), without the needle (210) being touched by human hands. The plunger (224) retracts the needle (210) completely back inside the cartridge (202), again without the needle (210) being touched by human hands and further releases the plunger (224) from the second compartment (204) to enable removal of the cartridge (202) from the barrel shaped portion (214) of the syringe to thereby enable the insertion of a fresh cartridge (202) into the barrel shaped portion (214) of the syringe in preparation for the next injection.

11 Claims, 7 Drawing Sheets

DISPOSABLE HYPODERMIC NEEDLE AND MEDICATION CARTRIDGE

BACKGROUND OF THE INVENTION

This invention relates generally to safe hypodermic syringes and more particularly to safe, reusable hypodermic syringes employing a hermetically sealed disposable cartridge containing both medication and a hollow hypodermic needle cannula which is exposable externally of said syringe only during the injection of the medication into a patient and which is then retractable completely back into the cartridge after the injection, with the cartridge and the needle contained therein being immediately disposable, with the entire process requiring the use of only one hand of the operator.

Hypodermic syringes of the type having a hollow needle cannula open at both ends and a pre-filled cartridge of fluid medication for injecting such medication from the cartridge to a targeted tissue area of a patient are well known in the art. However, before or after the injection, the needle is typically locked in an axially extended position projecting outwardly from a distal bore formed through the syringe cylinder.

In many cases, the needle is injected into a patient having a communicable disease such as AIDS or hepatitis. Prior to the disposing of the needle, or both the syringe and the needle, the hypodermic needle frequently must be removed from the syringe and broken or destroyed to prevent reuse. Dentists, doctors, nurses, and other health care workers are especially susceptible to accidental and potentially infectious needle strikes due to the careless handling or breaking of the needle and disposing of the needle after use.

The most life-threatening of the communicable diseases is AIDS. AIDS can be contracted by accidental puncture wound from a contaminated needle. This can occur by several methods:
1. Attempting to recap a contaminated needle.
2. Disposal of a needle in a non-rigid container.
3. Transfer of a syringe between health care personnel.

The current method of syringe preparation, injection and disposal is normally as follows:
1. A plastic capped needle is threaded onto a syringe.
2. A glass cartridge (with medication) is loaded into the syringe or alternatively medication is drawn into a syringe from a multidose vial.
3. The plastic cap is removed and the needle is exposed and inserted into the patient.
4. The injection is given.
5. The syringe (with the exposed contaminated needle) is passed to an assistant.
6. The assistant disposes of the needle.

Such accidental needle strikes typically require a blood test for such diseases as AIDS and hepatitis. The corresponding cost and inefficiency of testing medical workers who have received such an accidental needle strike can be considerable, which may be particularly damaging to a medical facility which is striving for economy. Should the patient be infected with the HIV virus then the person pricked with the needle contaminated by the infected patient has an extremely high risk of eventually dying from AIDS. Further, such accidental pricking could result in expensive personal liability to the facility in which the pricking occurred.

OBJECTS OF THE INVENTION

A primary object of the present invention is to provide safe hypodermic syringes employing a non-reusable, hermetically sealed, and disposable rigid cartridge assembly, sometimes herein referred to simply as the cartridge, containing both the medication and a hollow needle cannula and in which the needle can be projected out of the syringe to enable injection of the medication into the patient and then be completely retracted back into the cartridge after injection, all being done without the operator's hand ever coming near the needle and all being done with the use of only one of the operator's hands.

Another object of the invention is that the needle is completely and securely enclosed in the rigid cartridge at all times except during use thereof, thus preventing accidental pricking and unauthorized multiple use.

A third object of the invention is to insure that the health care worker need neither manually attach either a capped or uncapped needle to a syringe or cartridge, nor manually remove a needle, either capped or uncapped, from a syringe or cartridge, nor transfer a needle, capped or uncapped, to another person.

Another object of the invention is that the needle can be both extended for injection and retracted for disposal by the person giving the injection without such person touching the needle.

A fifth object of the invention is to provide means for safe disposal of the contaminated needle including non-exposure of the needle to sanitation workers handling trash since the used needle is contained completely in the rigid cartridge.

A sixth object is that the health care worker need not attach a needle to a syringe or to the cartridge nor does the needle need to be capped or recapped.

A seventh object of the invention is that the cartridge is usable either as a disposable cartridge for use in a syringe or as a separate disposable, single use syringe with its own plunger.

An eighth object of the invention is to prohibit the cartridge from being used more than once, thus reducing the spread of disease by multiple use.

Another object of the invention is the improvement of the safe use of hypodermic syringes and needles, generally.

BRIEF STATEMENT OF THE INVENTION

In accordance with one preferred form of the invention there is provided a reusable hypodermic syringe apparatus for injecting medication into a patient and comprising a barrel-like body having an opening therein for inserting and removing a disposable cartridge and an axially movable plunger for applying force to said cartridge, an improved cartridge insertable into the barrel-like body of the syringe through the opening therein to be substantially axially aligned with the axial motion of said plunger, a first medication-containing sealed compartment formed within the cartridge between first and second flexible seals each slidable within the cartridge to initially form a rigid cylindrical section due to the imcompressible medication between the seals and with the first seal being positioned in the path of the distal end of the plunger and partially penetrable by the distal end of the plunger as the plunger is moved into the cartridge. A second sealed compartment is formed within the cartridge between the second seal and the distal end of the cartridge and axially adjacent and in tandem with the first compartment and comprising therein a hypodermic needle cannula aligned substantially with the axial motion of the plunger. The first and second compartments are responsive to the insertion of the plunger against the first seal causing the first and second compartments to move as a unit in the cartridge to push the distal end of the needle out the end of the barrel-like body and to push the proximal end of the needle back into the first compartment to enable flow of medication from the first compartment through the hollow needle and into the patient. A connecting device connects together the needle, the first and second seals, and the plunger when injection of the medication into the patient has been completed. The connected-together needle and the first and second seals are responsive to the withdrawal of the plunger to be collectively retracted completely within the cartridge, and to separate the plunger from the first seal for subsequent removal of the cartridge and its contained used needle and seals from the barrel-like body of the syringe.

In accordance with a second, modified form of the invention a female threaded, enlarged finger grippable element is attachable to and removable from, the mating male threaded proximal end of the barrel-like portion of the syringe, thereby either closing or exposing the open proximal end of the barrel-like portion of the syringe so that the used cartridge can be disposed of simply by removing the enlarged element and holding the now open end of the barrel-like portion of the syringe over a suitable waste disposal container. In the above described embodiment of the invention a new, unused cartridge can then be inserted into the open proximal end of the barrel-like portion of the syringe and the threaded, hand grippable element, with the plunger 224 inserted therethrough, is then threaded back onto the mating threaded proximal end of the barrel-like portion of the reusable syringe to secure the new cartridge therein.

In accordance with a third, disposable form of the invention the syringe and the cartridge are combined into a single, unified cartridge-syringe structure having a single wall cylinder forming one portion thereof with the needle cannula and the medication being contained in separate compartments therein, as described generally above, and with an enlarged finger-grippable element being permanently formed on the proximal end of the unified cartridge-syringe structure. A plunger with a barbed distal end is insertable through an opening in the enlarged finger-grippable element and is securable to the proximal seal of the medication-containing compartment to initiate and complete the injection of medication into the patient in the manner described above with respect to the first embodiment of the invention. Upon completion of injection of the medication the plunger is completely withdrawn from the unified cartridge-syringe structure and then reused with a new cartridge-syringe structure. The used unified cartridge-syringe structure with the used needle safely contained therein is deposed of in an appropriately safe manner.

In accordance with a primary feature of the invention the medication and the hollow needle cannula are both entirely and safely contained within the cartridge immediately prior to the injection of the medication into the patient. Immediately after the injection of the medication into the patient, the plunger is withdrawn from the barrel-like body of the hypodermic syringe and the cartridge, and the hollow needle cannula is safely withdrawn from the patient and safely retracted into the cartridge.

Another feature of the invention is the use of barb-shaped, frictional, mechanical, magnetic, or other interlocking means between the distal end of the plunger and the first seal as well as between the first and second seals in first compartment of the cartridge with the distal end of the plunger being formed to engage, but not penetrate through, the first seal of the first compartment and with the shaped proximal end of the needle cannula being formed to penetrate through the second seal and into the first seal after the injection has been completed to connect together the needle cannula, the first and second seals of the first compartment, and the plunger so that as the plunger is retracted, the needle cannula, and the first and second seals will all be completely retracted into the cartridge.

A third feature of the invention is the use of a needle stop mechanism to limit the amount of the projection of the distal end of the needle cannula out of the cartridge and the barrel-like body of the hypodermic syringe and with the second seal being of a material which will push the distal end of the needle towards the sterile seal 216 of the cartridge in the barrel-like body without significant penetration of the second seal by the proximal end of needle until the forward motion of the needle is stopped by the needle stop mechanism, at which time the proximal end of the needle cannula will penetrate through the second seal and into the medication-containing first compartment to enable flow of the medication through the hollow needle cannula and into the patient.

Another feature of the invention is a plunger having a finger or hand grip formed on the proximal end thereof and a finger or hand grip (an enlarged element) on the proximal end of the barrel-like body of the syringe to enable good control of the plunger, including the ability to aspirate the patient's body fluid in a manner whereby the plunger is partially retracted to withdraw a small amount of the patient's body fluid back into the first compartment, thereby determining if the needle was inserted into the proper target tissue of the patient.

A fifth feature of the invention is a second stop mechanism which limits the movement of the secured-together needle cannula and the first and second seals towards the proximal end of the barrel-like body of the syringe so that the needle and the seals remain entirely within the cartridge but permitting further movement of the plunger to disengage the distal end of the plunger from the first seal of the first compartment.

A sixth feature of the invention is that the cartridge can be inserted into the syringe (in the first and second embodiments of the invention in which the syringe and the cartridge are separable components of the invention) either in an opening in the side of the barrel-like body of the syringe or in the proximal end of the syringe when the finger grippable element is removed (unthreaded) from the threaded, proximal end of the barrel-like body of the syringe.

A seventh feature of the third embodiment of the invention is that the plunger is completely retractable from the remainder of the hypodermic syringe and cartridge, which are disposable, and the subsequent reuse of the plunger.

Figure 1:
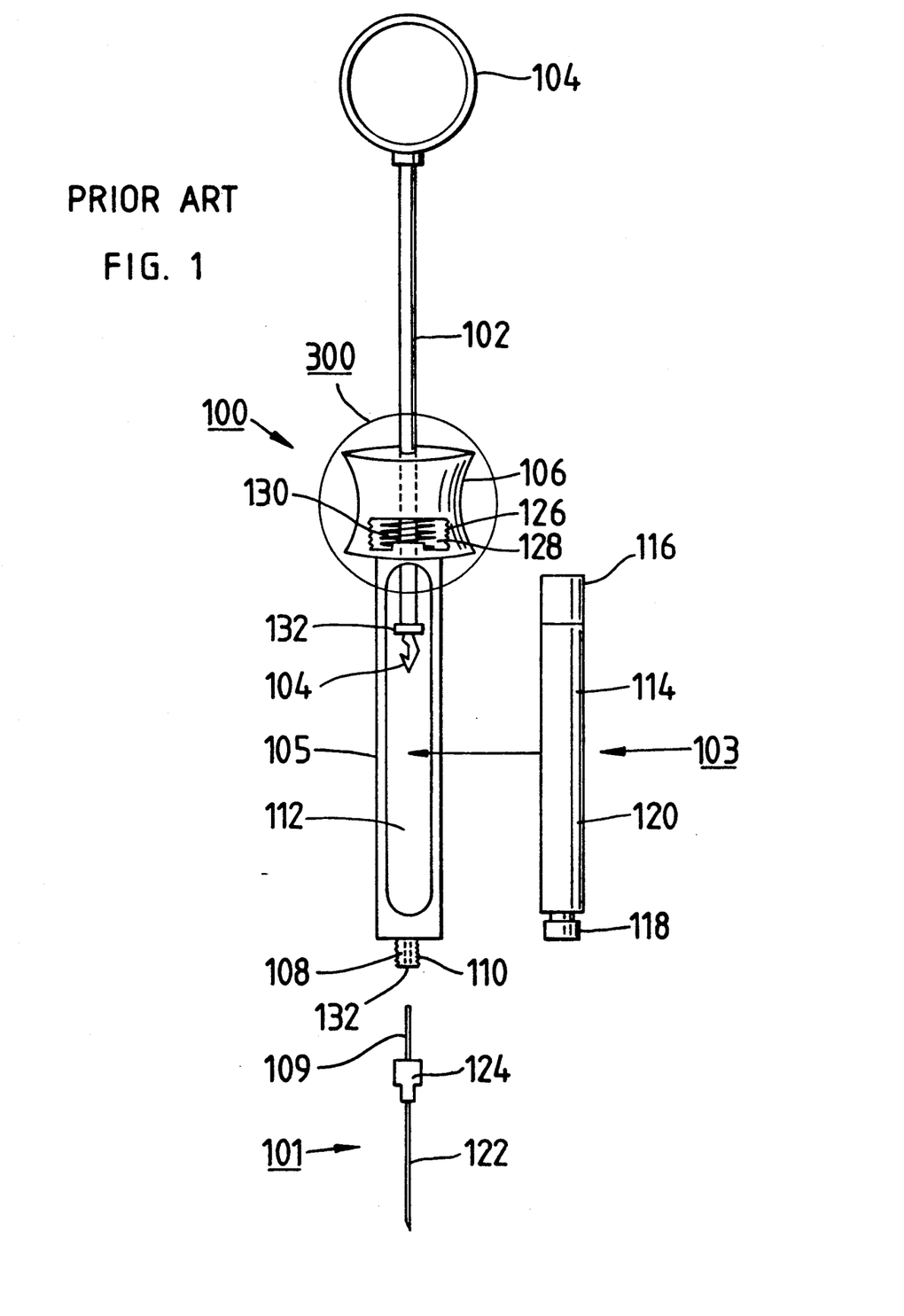
FIG. 1 shows a prior art hypodermic syringe employing a cartridge which has been pre-filled with medication.

The above objects and features of the invention will be more fully understood from the following detailed discussion thereof when read in conjunction with the drawings in which:

DISCUSSION OF SOME RELEVANT PRIOR ART (FIG.I)

Referring now to FIG. 1 a current prior art hypodermic syringe shown therein is comprised of three principal parts: (a) the syringe 100 (including plunger 102) which can be of metal or other suitable material such as, for example, selected plastics, (b) the screw on, hollow hypodermic needle 101, and the cartridge 103 containing the medication.

To assemble the above-mentioned three principal parts of the prior art syringe of FIG. 1, the proximal end 109 of needle 101 is inserted through aperture 132 of externally threaded (110) tip 108 of syringe 100 and secured thereon by internally threaded needle hub 124. Then, while the cartridge 103 is held near the slot 112 of syringe 100 the barbed distal end 122 of plunger 102 is forcefully retracted against spring 130 and the cartridge 103 is inserted into the slot 112.

When the plunger 102 is released it is then forced downwardly into the slotted barrel 105 of the syringe by spring 130 so that the barbed end 104 of plunger 102 grippably engages but does not penetrate through the rubber-like seal 116 of cartridge 103, thereby firmly securing the cartridge 103 securely within the body 105 of syringe 100. Simultaneously, the proximal end 109 of needle 122 penetrates the rubber-like seal 118 of cartridge 103 to enable the flow of the medication within the cartridge 103 to flow through the needle 101 and into the patient as plunger 102 is inserted farther into the syringe and against rubber-like seal 116 to force the seal 116 down into the cartridge 103 to in turn force the medication 120 out of cartridge 103, and through needle cannula 101 into the patient. More specifically, when plunger 102 is pressed against the rubber seal 116, which is slidable within the cartridge 103, the rubber seal 116 will force the medication out of chamber 114, through hollow needle 101 and into the patient.

Forceable retraction of plunger 102 so that collar 132 is drawn back to compress spring 130 will cause the barbed end 104 of plunger 102 to be retracted out of rubber-like seal 116 to enable easy removal of cartridge 103 from the syringe 100 through opening 112.

It is to be specifically noted, however, that at all times during the above described process of installing the needle 101 in the cartridge 103 within the syringe body 105, and the process of removing the cartridge 103 and the contaminated needle 101, from syringe body 105, the contaminated needle 101 is exposed, thereby creating a risk of some person being pricked by such contaminated needle 101. If the patient had contracted the HIV or the AIDS virus, the person accidentally pricked by the needle would almost certainly also contract the HIV virus or the AIDS virus.

As set forth above the present invention almost literally prevents such accidental pricking as will become evident from the discussion of FIGS. 2 through 9 set forth herein.

DETAILED DESCRIPTION OF THREE FORMS OF THE INVENTION

A—First Preferred Embodiment of the Invention (FIGS. 2-9)

Figure 2:
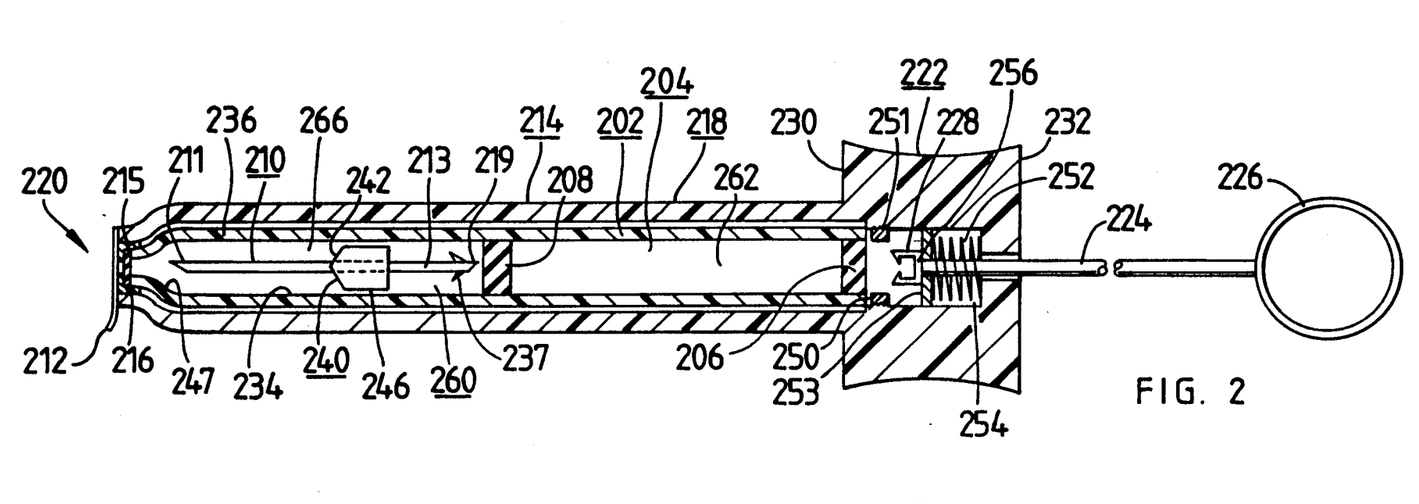
FIG. 2 shows a longitudinal sectional view of the first form of the present invention prior to the use thereof, including both the syringe and the cartridge.
Figure 3:
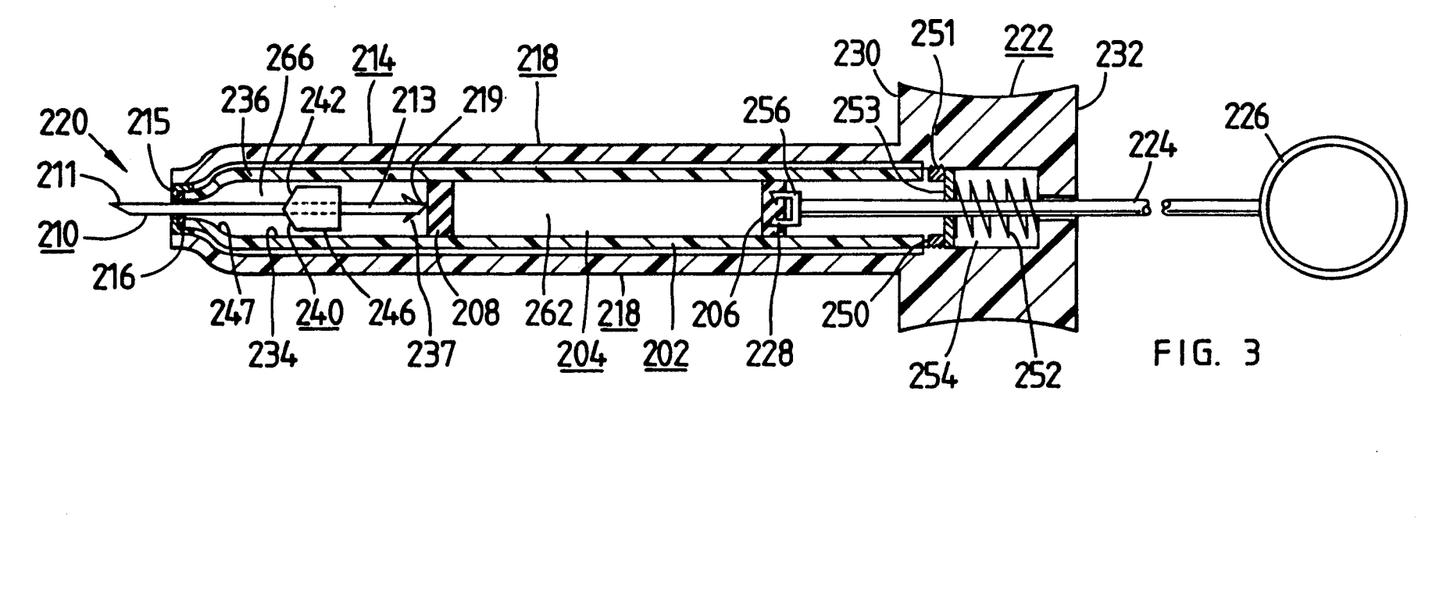
FIG. 3 shows a longitudinal sectional view of the invention after the plunger has been inserted sufficiently to engage and push the first, initially rigid, compartment towards the barbed proximal end of the needle so that the barbed proximal end of the needle is pressed against, but not through the second seal of the first compartment and the distal end of the needle is pushed partially out of the distal end of the syringe.
Figure 4:
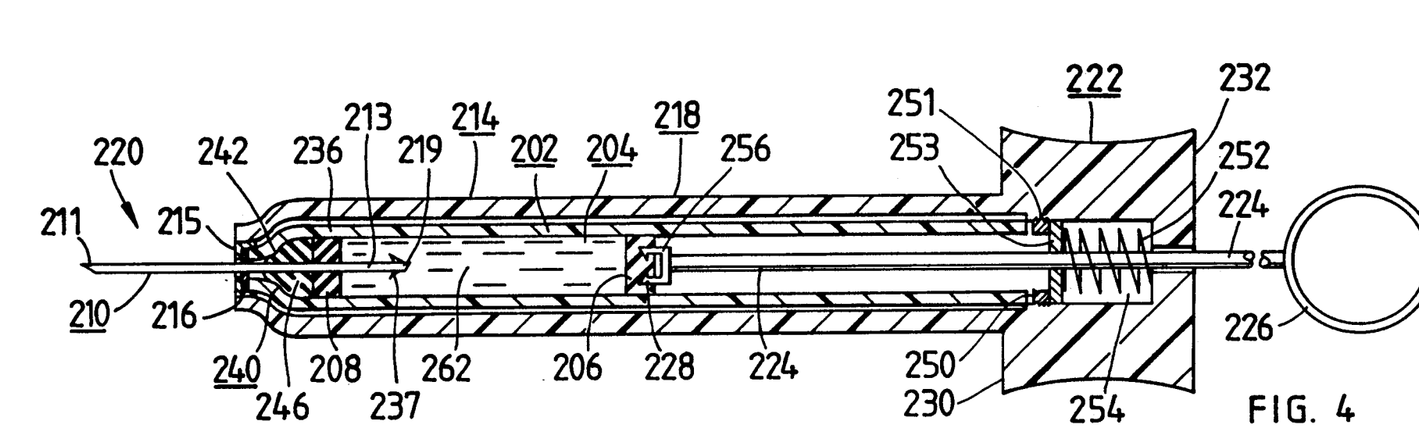
FIG. 4 shows the plunger inserted farther into the cartridge to push the distal end of the needle completely out of the end of the syringe and the barbed proximal end of the needle completely through the second seal of the first compartment and into the medication.

Referring now to FIG. 2 there is shown a sectional view of the present invention taken along the axis of the improved hypodermic syringe assembly 218, with the cartridge 202 in syringe 218 containing both the medication 262 and the needle cannula 210 already inserted into the barrel-like body portion 214 of the hypodermic syringe 218 and before the use of the syringe has been initiated.

In FIG. 2 which shows the major view of the invention, the syringe 218, (excluding the cartridge 202 which contains the medication 262, the first seal 206, the second seal 208, the needle 210, the membrane seal 212, and a metal rim 215 holding a rubber-like seal 216 securely over the distal opening of cartridge 202), comprises a hollow, barrel-like body 214 with an elongated opening 280 in the side thereof (not shown in FIG. 2 but shown in FIG. 8) for insertion and removal of the cartridge 202, and a small opening 220 in the extreme distal end of the barrel-like body 214 to enable passage of the needle 210 from within the cartridge 202, through the membrane 216 and the opening 220 to be exposed externally of the syringe for injection into the patient. Also shown in FIG. 2 is an enlarged portion 222 which includes an inner cavity 254 which enable several functions to be performed in connection with the plunger 224, the plunger ring 226, the barbed end 228 of the plunger 224, and the action of the cartridge 202, as discussed generally below.

The vertical surface area 230 of enlarged element 222 is sufficiently large for an operator to place his first and second fingers on either side of syringe body 218, with his thumb in ring 226, in order to push the barbed end 228 of plunger 224 towards and into, but not through, the rubber-like seal 206 of cartridge 202. During retraction of the plunger 224 the operator's index finger and the adjacent finger are positioned on either side of the plunger 224 and on area 232 with his thumb in ring 226. The function of annular washer 253, compression spring 252 and annular flange 251 will be described in detail in the discussion of FIG. 7. Generally the afore-mentioned elements enable the separation of seal 206 and the barbed end 228 of plunger 224.

At this point a discussion of the co-action between the hypodermic syringe 218 and the cartridge 202 will be set forth. Since the first and second seals 206 and 208 are slidable but sealably engaged with the inner surface 234 of the tubular portion 236 of cartridge 202, the section of the tubular element 236 of cartridge 202 between the seals 208 and 206, which is filled with a virtually incompressible medication 262, will act as a rigid rod. Thus, as the barbed end 228 of plunger 224 is inserted farther against the rubber-like first seal 206, the second seal 208 will move in unison with seal 206 towards the barbed, proximal end 237 of needle 210.

Figure 5:
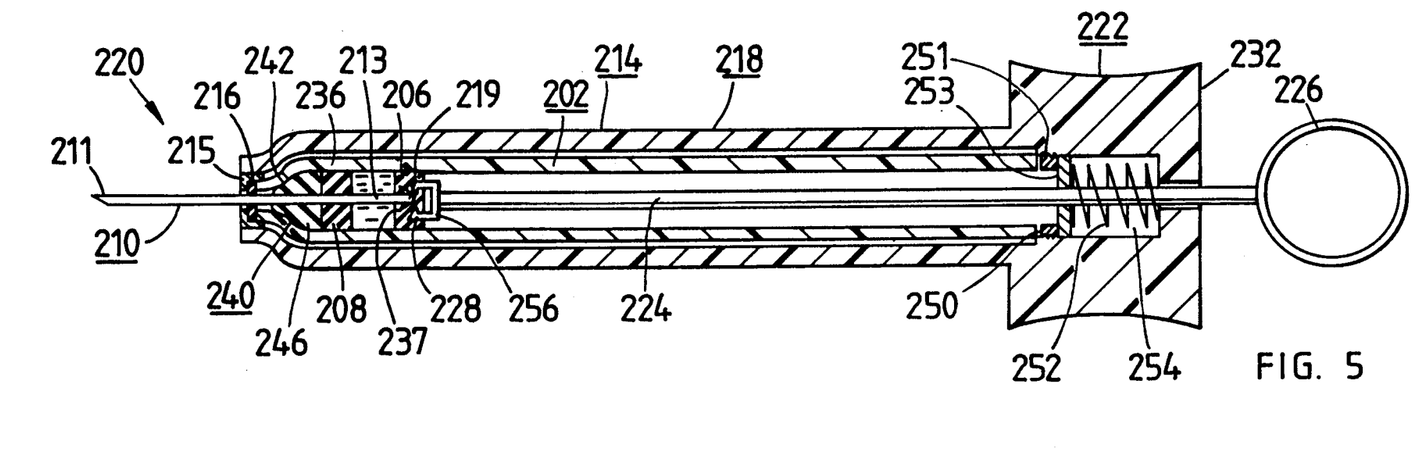
FIG. 5 shows the plunger inserted to its fullest extent with the needle fully exposed and the injection completed.

The barbed, proximal end 237 of needle 210 is designed to ultimately penetrate through the second rubber-like seal 208 and into the compartment 204 containing the medication 262, but not until the movement of seal 208 has pushed the front, tapered end 242 of needle hub 240 forward into the divergently shaped end 247 of the distal end of cartridge 202 and the flat, vertical surface 238 of needle hub 240 abuts against seal 208, as shown in FIG. 5.

It is to be noted that needle hub 240 (which is axially secured to and concentric with needle 210) has a large diameter section 246 which forms a third seal and slidably engages the inner surface 234 of the tubular section 236 of cartridge 202 to maintain the needle 210 in substantial axial alignment with the aperture 220 at the distal end of the barrel-like body 214 of the syringe 218 and with the axial motion of plunger 224.

After the barbed end 237 of needle 210 penetrates completely through and somewhat beyond the seal 208 the medication entrance aperture 219, will be positioned within the medication 262 in the extreme proximal end of needle 210 and consequently will allow the medication 262 to flow through the aperture 219 and then through the hollow needle cannula 210 and into the patient.

Continued insertion of the plunger 224 against the first seal 206 will cause continuing injection of the medication into the patient until the chamber 204, initially containing the medication 262, is virtually empty. As shown in FIG. 5, seals 206 and 208 are positioned close together, and the proximal, barbed end 237 of needle 210 has penetrated not only completely through the second seal 208 but also into the first seal 206, also as shown in FIG. 5, so that the needle 210, the seals 208 and 206, and the plunger 224 (by means of its barbed end being inserted into seal 206) are all connected together. Thus, when plunger 224 is withdrawn from the barrel-like body 214 of the syringe 218 the connected-together assembly of the needle 210 and the seals 208 and 206 will be withdrawn back into the tubular-like element 236 (i.e. the cartridge 202).

Figure 6:
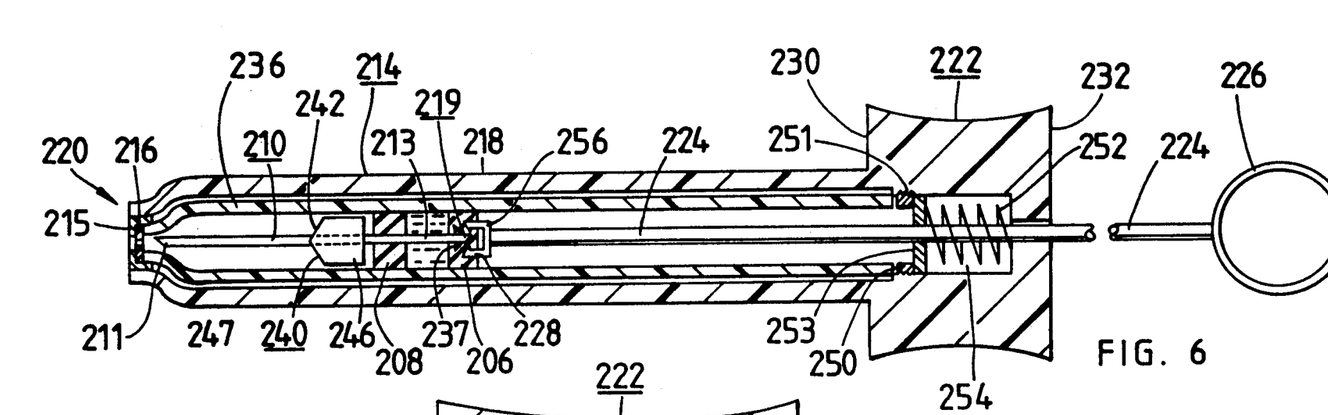
FIG. 6 shows the plunger partially retracted and pulling with it into the cartridge the needle and the first and second seals.

It is to be noted the needle 210 and the seals 208 and 206 will be retracted, as shown in FIG. 6, until they are completely enclosed within the tubular element 236 of the cartridge 202 at which time their retractive motion will be stopped by the shoulder 250 of the annular ring 251 of the enlarged element 222. As shown in the enlarged view of FIG. 7, however, the plunger 224 can continue to be further withdrawn forcibly against the compression spring 252 which is positioned in the cavity 254 behind the annular washer 253 which in turn is positioned behind the shoulder 256 of the barbed distal end of plunger 224 and limited in its leftward motion (FIGS. 2 and 7) by the annular ring 251, which is threadedly engaged with the enlarged portion 222 of the syringe. Thus, the barbed end 228 of plunger 224 becomes disengaged from the seal 206. The cartridge 202 containing the used needle 210 and the two seals 208 and 206 can then easily, and with complete safety to the operator, be withdrawn from the barrel-like body 214 of the hypodermic syringe 218 through the elongated slot 280 shown in FIG. 8.

It is to be noted that a tab 212 (FIG. 2), which can be a peel-off foil tab or any other suitable sterile tab, initially is adhesively secured to the outside rim of the metal ring 215 as an additional sealing means and is peeled off immediately before the cartridge 202 is inserted into the barrel-like body 214 of the syringe 218. It is further to be noted that the cartridge 202 preferably is not inserted into the interior of the barrel-like body 214 of the syringe until just before injection of the medication into the patient.

As discussed generally above, the seal 216 of FIG. 2 forms the distal end of the needle containing compartment 260 within the cartridge 202, and the seal 208 forms not only the other end of compartment 260 but also forms the distal end of the compartment 204 of cartridge 202. The proximal end of compartment 204 is formed by seal 206.

Only the needle 210 and its hub 240, with sterile air space 266 therearound, is initially contained within the compartment 260 and only the medication 262 is initially contained within compartment 204. Although needle 210 will penetrate the seal 208 during injection of the medication into the patient no medication will flow into the now collapsed compartment 260 because the penetrated seal 208 will immediately reseal around the needle 210 which has penetrated therethrough.

Figure 7:
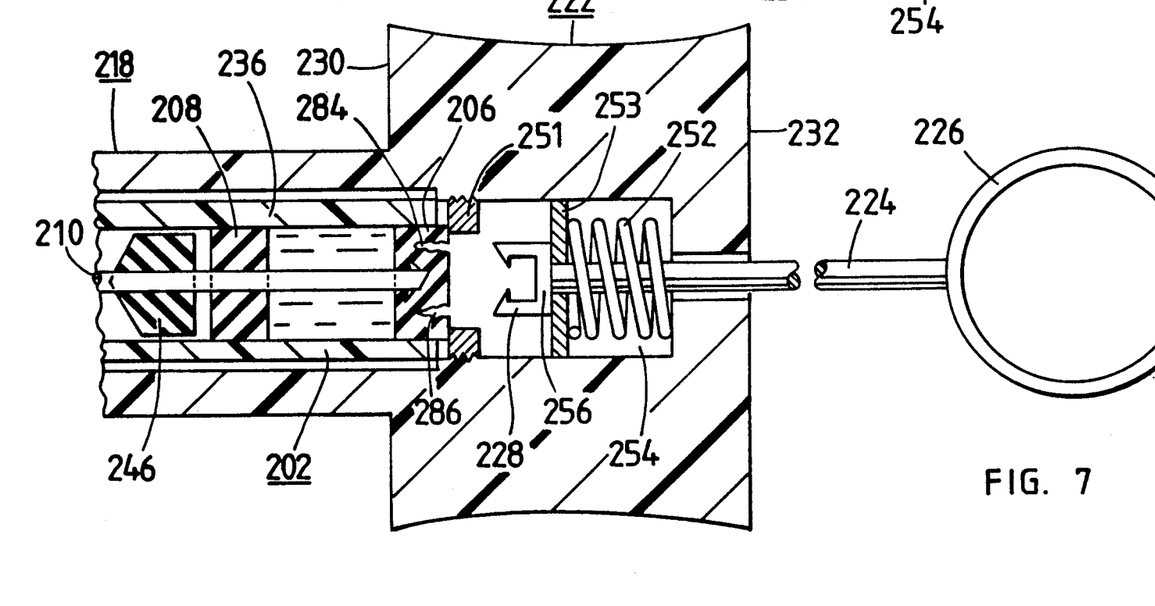
FIG. 7 is an enlarged view of the plunger retracted to the point where retractive movement of the first seal has been stopped by a shoulder formed on the syringe while the plunger has continued to retract to disengage the plunger from the first seal, thus enabling easy removal of the cartridge containing the used needle and seals.

As indicated generally above, FIGS. 3, 4, 5, 6, and 7 show the relationship of the various parts of invention as the plunger 224 is gradually inserted farther into the tubular-like element 236 of the cartridge 202 thereby pushing the seal 206 to the left in FIGS. 2–5, and finally retracting the plunger 224 out of the barrel-like body 214 of the syringe and the connected-together used needle 210 and the seals 208 and 206 back into the tubular shaped element 236 of the cartridge 202, as shown in FIGS. 6 and 7.

Figure 8:
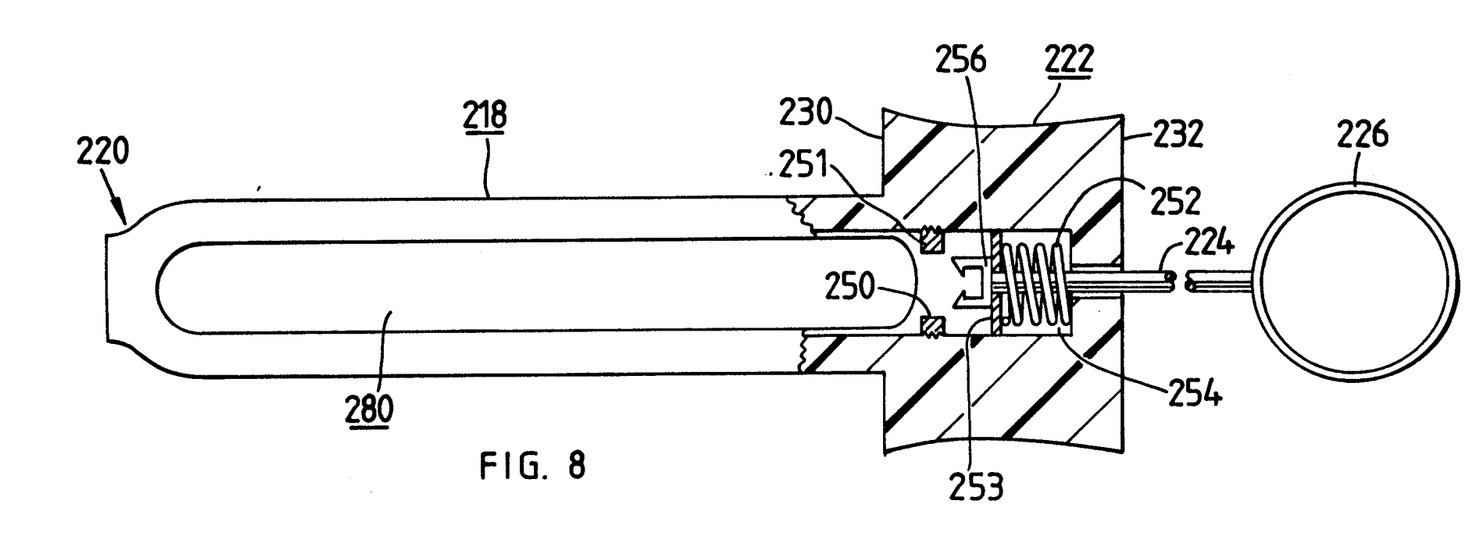
FIG. 8 shows one form of opening in the wall of the barrel-like portion of the syringe into which the cartridge of FIG. 9 can be inserted and removed, and also shows the spring mechanism which allows the plunger to be retracted sufficiently to enable insertion and removal of the cartridge.
Figure 9:
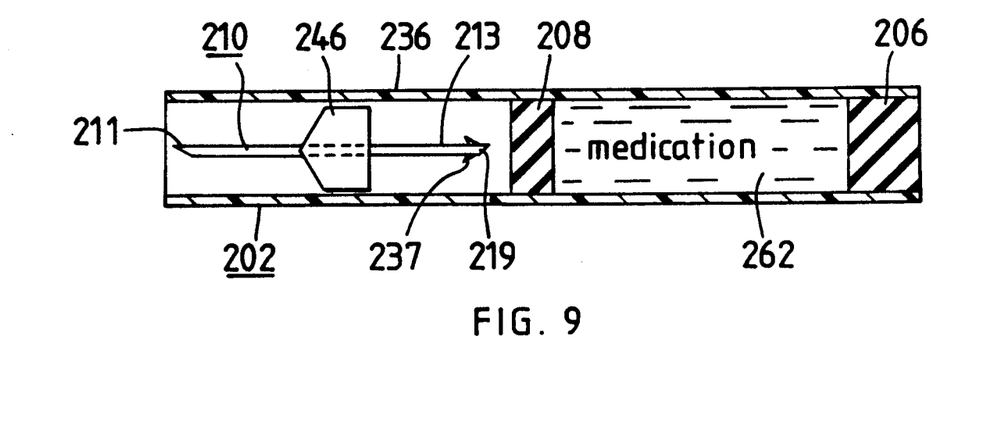
FIG. 9 shows a sectional view of the cartridge which is inserted into the opening of the syringe of FIG. 8.

Also, as discussed briefly above, the plunger 224 can be retracted farther than the seal 206, as shown in detail in enlarged in FIG. 7, thus disengaging the barbed end 228 of the plunger 224 from the seal 206 to enable easy removal of the cartridge 202 from the opening 280 of the syringe 218 as shown in FIG. 8.

Referring now in more detail to the enlarged drawing of FIG. 7, the barbed distal end 228 of plunger 224 is retracted against the washer-like element 253 which compresses the spring element 252 as the operator forcibly retracts the plunger ring 226 to cause the barbed end 228 of plunger 224 to disengage from seal 206. The seal 206 and the tubular element 236 of the cartridge 202 are blocked by annular element 251 and thus prevented from moving with the plunger 224 as the plunger is retracted from seal 206.

The used needle 210, the needle hub 240, and the seals 206 and 208 can all be seen to have been moved to the right within the tubular element 236 of the cartridge 202 as a connected-together group, as shown in FIG. 7. The two apertures 284 and 286 represent the holes left in seal 206 as the barbed end 228 of plunger 224 is pulled forcibly from the first seal 206 by the operator.

B-A Second Form of the Invention

Figure 10:
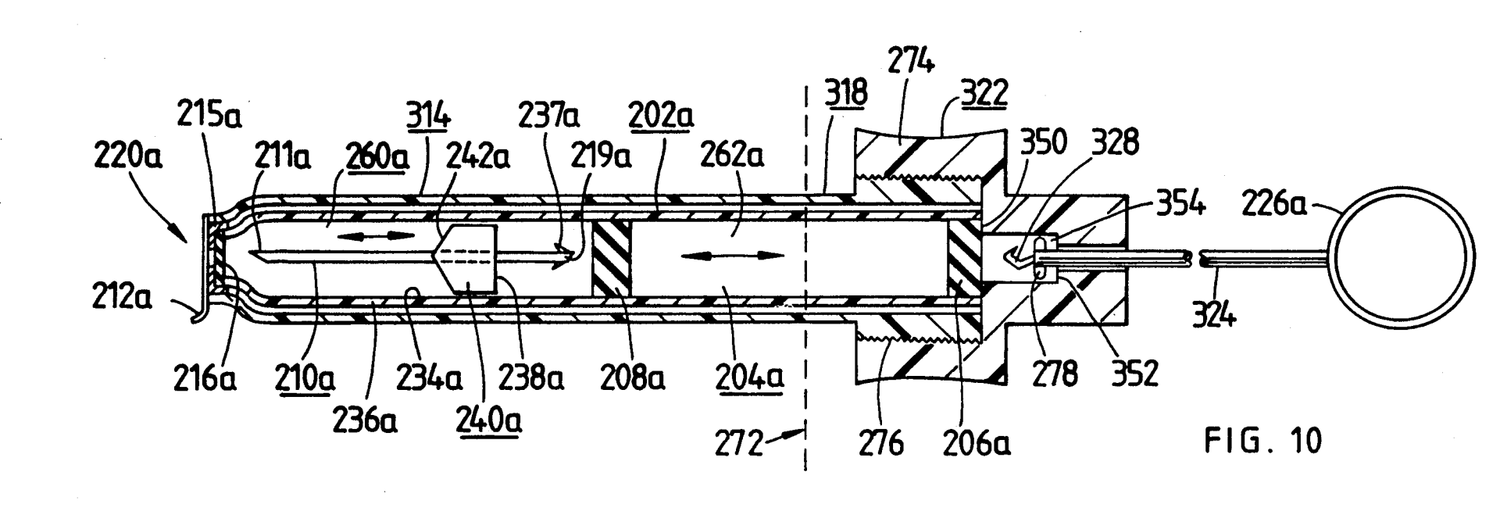
FIGS. 10 and 11 show a second embodiment of the invention in different stages of operation.

Referring now to FIGS. 10-14 there is shown the second form of the invention wherein a cartridge 202a is inserted and removed from the syringe 318 of FIG. 10 through an opening in the proximal end (FIG. 12) of the syringe 318 before and after the injection of the medication into the patient has been completed.

Much of the structure of FIG. 10 is similar to that of FIG. 2 and corresponding parts are designated by the same numerical reference characters but with the corresponding reference characters of FIG. 10 being followed by the letter "a". Thus, needle 210 of FIG. 2 becomes needle 210a of FIG. 10. Non-corresponding parts have new reference characters in FIGS. 10-14.

The principal differences of the structures of FIGS. 2 and 10-14 lie to the right of the vertical dotted line 272 in FIG. 10. More specifically the enlarged finger-grippable element 322 of FIG. 10 is quite different from the enlarged finger grippable element 222 FIG. 2 in several respects. For example, in FIG. 10 the enlarged finger-grippable element 322 has a female threaded portion 274 which mates with the male threaded portion 276 of the proximal end of the barrel-like portion 314 of the syringe 318 so that the entire finger grippable element 322 along with the plunger 324, which is part of the syringe 318, can be removed from the barrel-like portion 314 of syringe 318 and a cartridge 202a either removed (after injection) or inserted (before injection) into the barrel-like portion 314 of the syringe 318.

Further, in FIG. 10 a rubber-like annular element (ring) 278 is secured to the distal end of plunger 324 within the cavity 354 of the enlarged element 322 to allow the barbed distal end 328 of the plunger 324 to become completely disegaged from the seal 206a. The shoulder 352 of the enlarged element 322 prevents the plunger 324 from being removed from the enlarged element 322.

Figure 12:
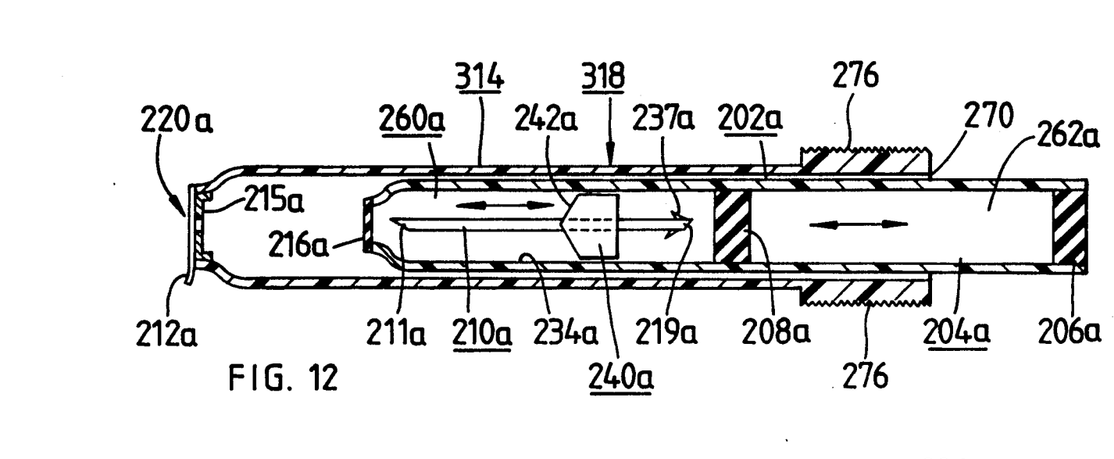
FIGS. 12-14 show the second embodiment of FIGS. 10 and 11 in disassembled form.
Figure 13:
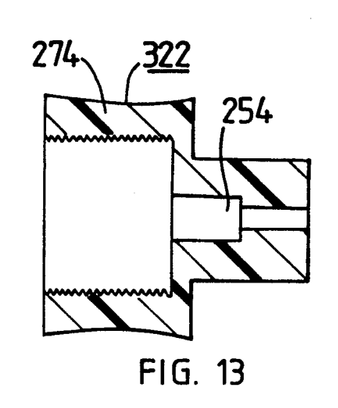
Figures 14, 15:
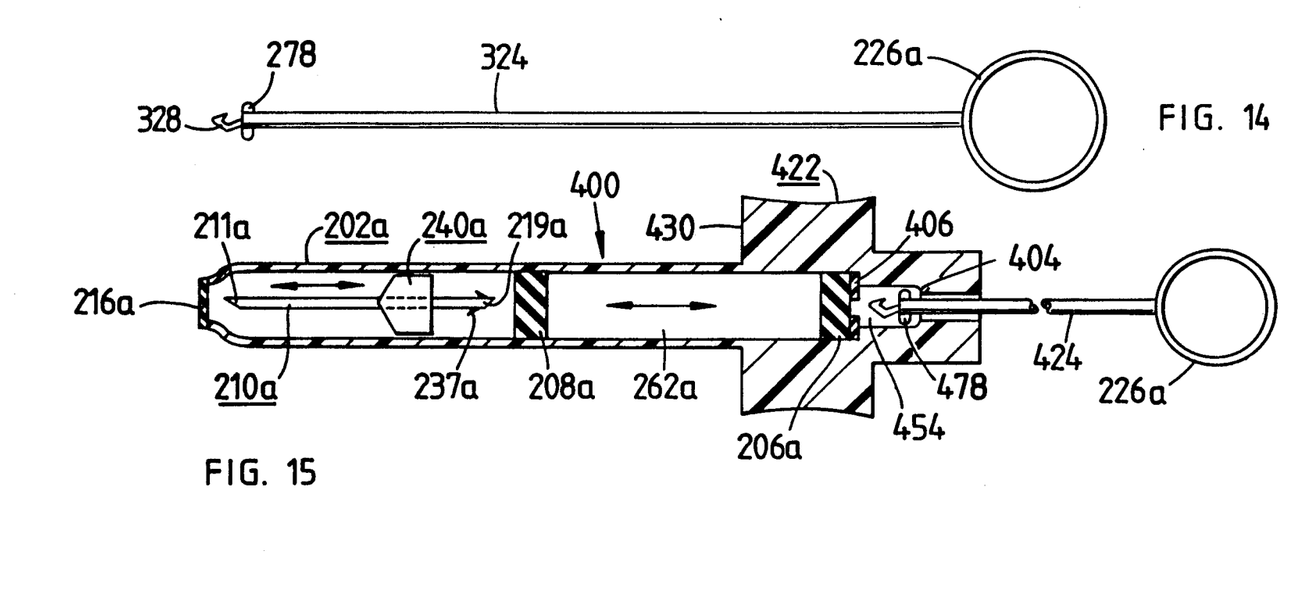
FIG. 15 shows a third, disposable form of the invention.

FIGS. 12, 13 and 14 show the disassembly of the cartridge 202a and the syringe 318 just before being loaded for injection. It is seen that the enlarged element 322 of the syringe 318 has been removed. For clarity, the plunger 324 has been shown as having been removed from enlarged element 322. In practice the plunger 324 is constrained to stay in the cavity 354 of the enlarged element 322 of syringe 318 by plunger stop 351 and the plunger stop shoulder 352 of the enlarged element 322. FIGS. 12, 13 and 14 also demonstrates how the cartridge 202a is removed through the open end drop 270 of the syringe 318 for disposal.

The operation of the device of FIG. 10 and especially the functioning and coaction of the plunger 324, the cartridge 202a, the seals 206a and 208a, and the needle 210a as shown in FIG. 10, are identical to the coactive operational steps of the plunger 224, the cartridge 202, the seals 206 and 208, and the needle 210 the of the first embodiment of FIG. 2, as shown in FIGS. 2, 3, 4, 5 and 6. Accordingly, the progressive operational steps of the embodiment of FIG. 10 will not be repeated except for FIG. 11 which shows the relation of the various elements of the embodiment of FIG. 10 when the reaction of the plunger of the embodiment of FIG. 10 has been completed.

Figure 11:
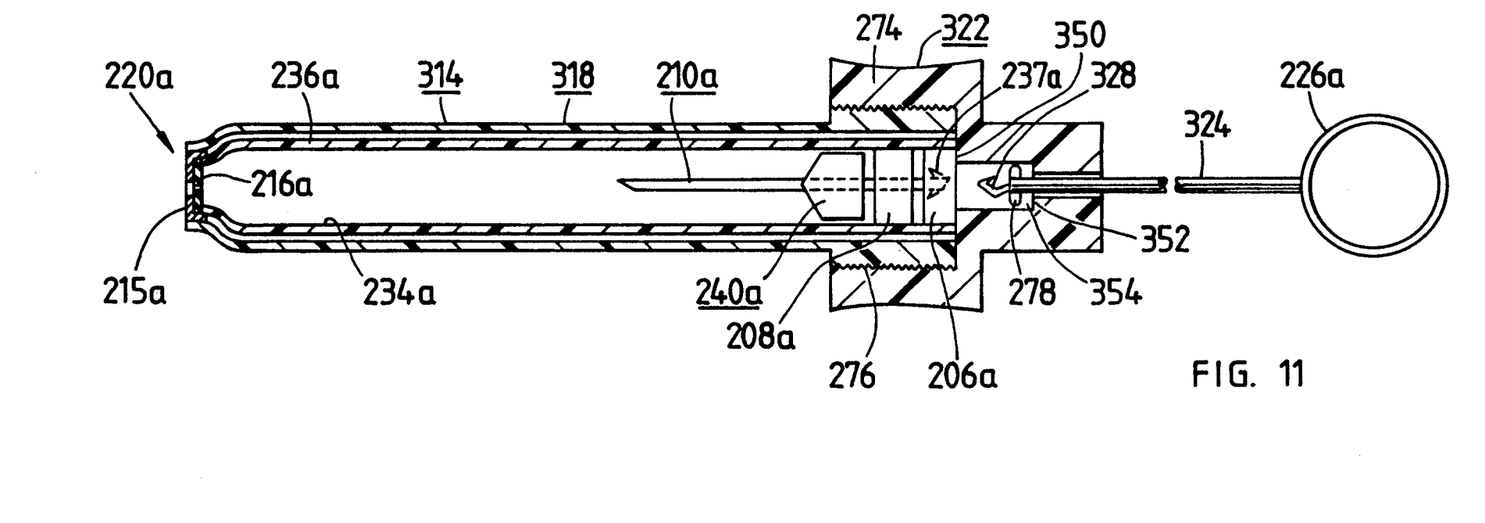

After the full retraction of plunger 324 as shown in FIG. 11 the connected-together seals 208a and 206a and the contaminated needle 210a are all completely contained in the cartridge 202a, and the barbed distal end 328 of plunger 324 has become disengaged from seal 206a whose retractive movement has been blocked by blocking element 350 to permit the barbed distal end 328 of plunger 324 to become completely retracted into the cavity 354 until the annular, rubber-like element 278 impacts against shoulder 352 of enlarged element 322 as discussed above.

C-A THIRD FORM OF THE INVENTION

Referring now to FIG. 15 there is shown a third form of the invention wherein the syringe (except for the plunger 424) and the cartridge are combined into a unitary cartridge-syringe structure 400 which is all completely disposable, except for the plunger 424, after the medication has been injected into the patient.

More specifically, in FIG. 15 the syringe portion has been reduced to an enlarged portion 422 which comprises a finger-grippable portion 430, a partial shoulder stop element 404 which provides only a partial resistance to the rubber-like annular plunger ring 478 from passing therethrough, thus allowing complete removal of the plunger 424 from the embodiment of FIG. 15, and a shoulder 206a which functions to completely contain seals 406 and 208a and needle 210a within the unified structure 400.

Upon completion of the injection of the medication into the patient the plunger 424 can then be completely withdrawn from the unified cartridge-syringe structure 400 and reused with another unified cartridge-syringe structure. The used unified cartridge-syringe structure can then be disposed of in an appropriate manner.

It is to be understood that the forms of the invention shown and described herein are but preferred embodiments thereof and that other modifications and improvements thereof can be made by one of ordinary skill in the art without the exercise of invention and without departing from the spirit or scope of the invention as defined in the appended claims. For example, some or all of the embodiments can be made of plastic, metal, or other suitable materials. With the use of plastic materials, however, disposable devices can be more easily fabricated.

Further, the present forms of the invention can be applied to the establishment of a multi-dose vial syringe without inventive modification.

We claim:

1. A hypodermic syringe assembly comprising of:

a tubular portion comprising both medication and a hollow needle cannula for injecting said medication into a patient;

proximal and distal sealed compartments, formed by the engagement of the interior portion of said tubular portion by slidable sealing means, said distal compartment being formed between distal end of said tubular portion and said proximal compartment for containing said medication and needle, respectively;

a plunger slidably and axially secured in a proximal end of said tubular portion to be insertable and engagable with a proximal end of said proximal sealed compartment to extend said needle out of said tubular portion of said hypodermic syringe assembly with a proximal end of said needle being urged into fluid communication with said proximal compartment immediately before said injection of said medication into a patient without said needle being touched by human hands; and means for arresting retraction of said plunger to enable the separation of said plunger from said tubular portion subsequent to retraction of said proximal compartment and said needle completely within said tubular portion to enable disposal of said tubular portion containing the contaminated needle and enabling reuse of said plunger.

2. In a hypodermic syringe assembly as in claim 1 in which said plunger comprises a ring on a proximal end thereof to enable an operator to easily insert and extract said plunger into and from said tubular portion in varying amounts to facilitate aspiration of small amounts of fluid from said patient to determine if said hollow needle has been targeted correctly in said patient.

3. A hypodermic syringe apparatus as in claim 1 in which said tubular portion comprises an enlarged element formed at the proximal end thereof and shaped to provide finger-grippable elements thereon to enable an operator to insert and retract said plunger from said tubular portion and further to cover most of the proximal end of said tubular portion with a bore therethrough to enable said plunger to pass therethrough to engage said first seal and to be completely withdrawn therefrom after injection of the medication into the patient to enable disposal of all of said hypodermic syringe assembly except said plunger.

4. A hypodermic syringe apparatus in claim 1 in which the distal end of said tubular portion is abruptly narrowed to form a short, cylindrical section substantially concentric with said tubular portion, and further comprising:

a peel-off tab placed over said short, cylindrical section to maintain sterility within said tubular portion until immediately before injection of said medication into said patient.

5. A hypodermic syringe assembly comprising in combination:

a tubular portion having coaxial openings at a proximal end thereof and at a distal end thereof, said distal end forming a reduced diameter for the opening thereat relative to the tubular portion intermediate said openings;

first and second sealing means mounted within said tubular portion intermediate said openings to define therein a first compartment for containing a substantially incompressible liquid medication between said first and second sealing means;

a hollow needle slidably mounted coaxially within said tubular portion between said distal opening and said first compartment for axial movement longitudinally of said tubular portion;

a plunger slidably mounted coaxially within said proximal opening and insertable and engagable with said first sealing means to concomitantly urge said first compartment axially along said tubular portion toward said distal end such that said first compartment urges said hollow needle to a position abutting said distal end and extending through said distal opening, said needle having a proximal end adapted to pierce said second sealing means to provide communication with said first compartment and the exterior of said tubular portion through said hollow needle, and to concomitantly retract said first and second sealing means and said needle axially along said tubular portion toward said proximal opening; and means for connecting said hollow needle to said first sealing means when said first sealing means is urged proximal said second sealing means and said hollow needle by said plunger.

6. A hypodermic syringe assembly as defined in claim 5 in which said hollow needle is supported by a needle hub slidably engagable with a inner wall of said tubular portion with said needle hub having a shape to maintain said hollow needle coaxially aligned with the opening in said distal end of said tubular portion.

7. A hypodermic syringe assembly as in claim 5 wherein said first and second sealing means are made of a flexible, rubber-like material slidably engaging an inner wall of said tubular portion.

8. A hypodermic syringe assembly as defined in claim 5 wherein said first and second sealing means are resealable elastomeric disc seals.

9. A hypodermic syringe assembly comprising in combination:

a tubular portion having coaxial openings at a proximal end thereof and at a distal end thereof, said distal end forming a reduced diameter for the opening thereat relative to the tubular portion intermediate said openings;

first and second sealing means mounted within said tubular portion intermediate said openings and engaging the interior thereof to define therein a first compartment for containing a substantially incompressible liquid medication between said first and second sealing means;

a hollow needle slidably mounted coaxially within said tubular portion between said distal opening and said first compartment for axial movement longitudinally of said tubular portion;

a plunger slidably mounted coaxially within said proximal openings and insertable and engagable with said first sealing means to concomitantly urge said first compartment axially along said tubular portion toward said distal end such that said first compartment urges said hollow needle to a position abutting said distal end and extending through said distal opening, said needle having a proximal end adapted to pierce said second sealing means to provide fluid communication with said first compartment and the exterior of said tubular portion through said hollow needle, and to concomitantly retract said first and second sealing means and said needle axially along said tubular portion toward said proximal opening; and means for connecting said hollow needle to said first sealing means when said first sealing means is urged proximal said second sealing means and said hollow needle by said plunger including a barb affixed to the outer surface of said needle at said proximal end thereof.

10. A hypodermic syringe assembly as in claim 9 in which said barb affixed to outer surface of said hollow needle is positioned in the path of said second sealing means so that as said plunger is inserted progressively farther into said tubular portion said second sealing means will make contact with said barb of said hollow needle; and an orifice at said proximal end of said hollow needle near said barb through which said liquid medication enters said hollow needle after said barb of said hollow needle has penetrated through said second sealing means to gradually empty said liquid medication out from said first compartment and to impale said first sealing means upon said barb of said hollow needle to connect together said hollow needle and said first and second sealing means into one unit;

said unit responsive to the retraction of said plunger to be retracted completely within said tubular portion; and a stop means for stopping the retraction of said unit before the full retraction capability of said plunger is attained to enable the separation of said first sealing means and plunger.

11. A hypodermic syringe assembly as defined in claim 9 wherein said hollow needle includes a needle hub slidably engagable with the inner wall of said tubular portion and having a shape to maintain said needle axially aligned with said distal opening.

* * * * *